United States Patent [19]

Ikekawa

[11] Patent Number: 4,868,165
[45] Date of Patent: Sep. 19, 1989

[54] 24,24-DIFLUORO-26,27-DIMETHYL-VITAMIN $D_3$ DERIVATIVES

[75] Inventor: Nobuo Ikekawa, Musashino, Japan

[73] Assignee: Taisho Pharmaceutical Co., Ltd., Tokyo, Japan

[21] Appl. No.: 868,741

[22] Filed: May 30, 1986

[30] Foreign Application Priority Data

May 30, 1985 [JP] Japan .................................. 60-117487

[51] Int. Cl.$^4$ ...................... A61K 31/59; A61K 31/56
[52] U.S. Cl. .................... 514/167; 260/397.2
[58] Field of Search ........................ 514/167; 260/397.2

[56] References Cited

U.S. PATENT DOCUMENTS

| | | | |
|---|---|---|---|
| 4,225,596 | 9/1980 | De Luca | 514/167 |
| 4,521,410 | 6/1985 | Holick et al. | 260/397.2 |

FOREIGN PATENT DOCUMENTS

| | | | |
|---|---|---|---|
| 0076857 | 6/1980 | Japan | 260/397.2 |
| 0111460 | 8/1980 | Japan | 260/397.2 |

OTHER PUBLICATIONS

Chemical Abstracts, vol. 103 (1985) #71584z; Sai et al.

Primary Examiner—Leonard Schenkman
Assistant Examiner—Joseph A. Lipovsky
Attorney, Agent, or Firm—Wenderoth, Lind & Ponack

[57] ABSTRACT

24,24-Difluoro-26,27-dimethylvitamin $D_3$ derivatives represented by formula:

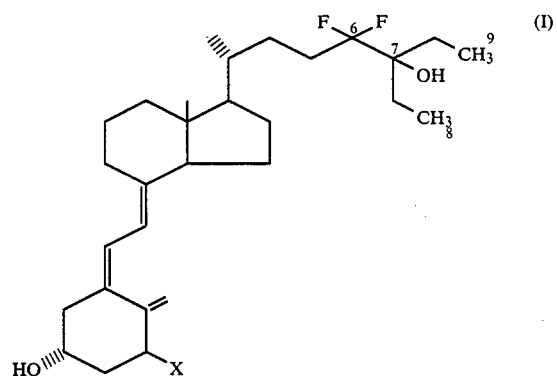

wherein X represents a hydrogen atom or a hydroxyl group. These compounds are prepared by irradiating 24,24-difluoro-26,27-dimethylcholesta-5,7-diene-(1α,)3β, 25-di- or triol with ultraviolet light, and is useful for the prevention or treatment of, for example, calcium pathobolism or osteoporosis.

3 Claims, No Drawings

24,24-DIFLUORO-26,27-DIMETHYLVITAMIN $D_3$ DERIVATIVES

This invention relates to derivatives of vitamin $D_3$ (i.e., cholecalciferol), and more specifically to 24,24-difluoro-26,27-dimethyl vitamin $D_3$ derivatives represented by the formula

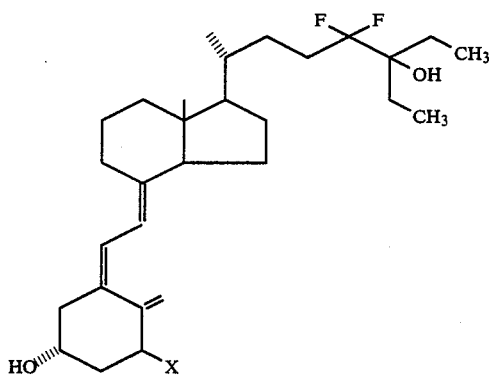

wherein X represents a hydrogen atom or a hydroxyl group, a process for production thereof, medicaments comprising the vitamin $D_3$ derivatives, and use of the derivatives as an active ingredient of medicaments for the prevention or treatment of diseases, such as calcium pathobolism and osteoporosis in particular.

Heretofore, the pharmacological effect of vitamin $D_3$ has been evaluated mainly with regard to its activity of increasing a calcium level in blood in animals with vitamin $D_3$ deficiency. But when it is used as a drug for improving bone symptoms in osteoporosis, renal failure and reduced function of the parathyroid gland, the blood calcium level increasing activity is not a direct activity, but is a secondary passive activity. Hypercalcemia is a side effect which appears during the treatment of the above diseases and requires the greatest caution. Frequently, it induces calcium deposition on the tissue and renal disorders, and the clinical doses of vitamin $D_3$ should therefore be restricted.

Accordingly, a compound having a strong activity of increasing the blood calcium level is not always useful in clinical applications. Clinical results can be anticipated more accurately by evaluating the biological activity of a vitamin $D_3$ derivative by using an animal disease model such as a rat osteoporosis model rather than evaluating it on the basis of the activity of increasing the blood calcium level.

When evaluated in regard to pharmacological effects and toxicity, vitamin $D_3$ derivatives proposed heretofore have not proved to be entirely satisfactory, and it is desired to develop new vitamin $D_3$ derivatives having strong bone forming activity.

The present inventor have extensively worked for vitamin $D_3$ derivatives having excellent pharmacological effects, particularly excellent bone forming activity, and low toxicity, and have now found that by introducing two fluorine atoms into the carbon atom at the 24-position of vitamin $D_3$ and a methyl group into the 26- and 27-positions respectively, novel vitamin $D_3$ derivatives can be obtained which in spite of their low toxicity, have a stronger bone forming activity than known 1,25-dihydroxy-26,27-dimethylvitamin $D_3$ and 1,25-dihydroxy-24,24-difluorovitamin $D_3$ in evaluations with a osteoporosis model.

Thus, according to this invention, there are provided 24,24-didluoro-26,27-dimethyl vitamin $D_3$ derivatives represented by the formula

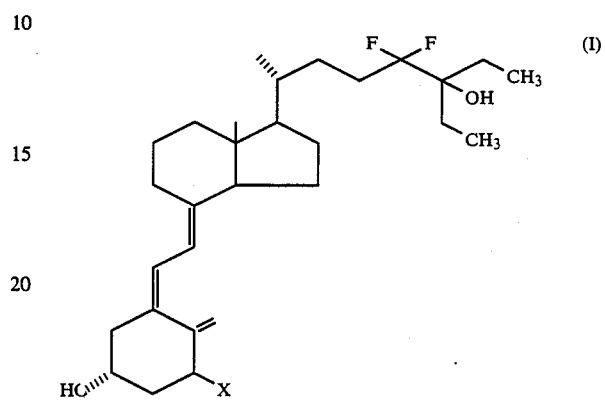

wherein X represents a hydrogen atom or a hydroxyl group as novel compounds.

The compound of formula (I) can be produced from compounds of formula (II) via the following reaction route.

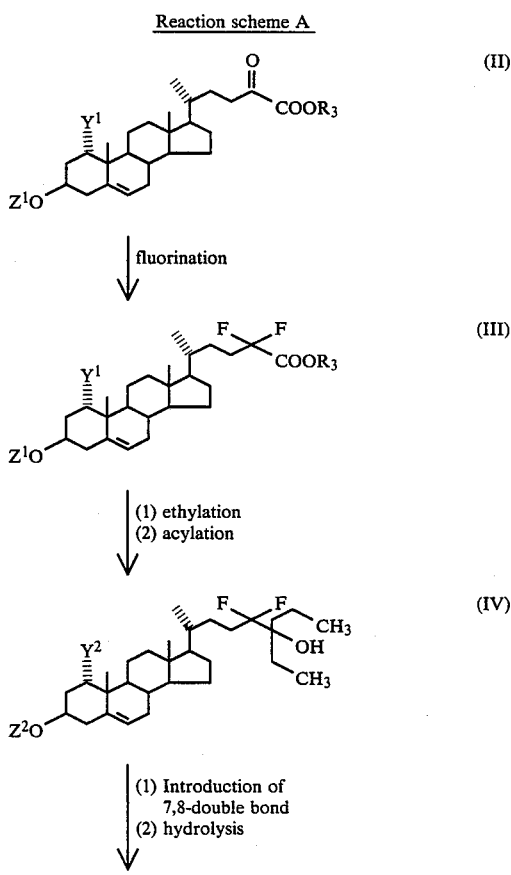

-continued
Reaction scheme A

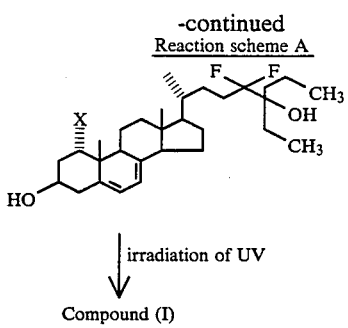

(V)

↓ irradiation of UV

Compound (I)

In the above formulae, $Y^1$ and $Y^2$ are identical or different and each erpresents a hydrogen atom or an acyloxy group;

$Z^1$ and $Z^2$ are identical or different and each epresents an acyl group;

R represents a lower alkyl group; and

X is as defined hereinabove.

The acyl moiety of the "acyloxy group" and the "acyl group" are, for example, lower alkanoyl groups such as formyl, acetyl, propionyl and butyryl groups, and aralkanoyl groups such as a benzoyl group. The "lower alkyl group" includes, for example, linear or branched alkyl groups such as methyl, ethyl, or propyl groups, the methyl group being especially preferred.

The term "lower", as used in the present specification and claims, means that a group or compound qualified by this term has not more than 6, preferably not more than 4, carbon atoms.

The fluorination of the compound of formula (II) is carried out by treating the compound of formula (II) with (diethylaminosulfur) trifluoride as a fluorinating agent usually in a suitable solvent such as dichloromethane to introduce two fluorine atoms into the carbon atom at the 24-positions. Generally, the fluorination is carried out at room temperature in an inert gaseous atmosphere.

The resulting compound of formula (III) is then ethylated. Usually, the ethylation is carried out by reacting the compound of formula (III) with ethyllithium in a solvent such as tetrahydrofuran in an inert gaseous atmosphere. By this ethylation, the alkanoyl group at the 3-position (when $Y^1$ at the 1-position is an alkanoyloxy group, its alkanoyl moiety as well) is split off simultaneously with the ethylation of the carbon atom at the 25-position to form a compound of the following compound.

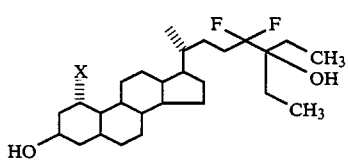

wherein X is as defined above. Hence, this compound is acylated in a customary manner to protect the hydroxyl group.

Thus, the compound of formula (IV) is obtained. Then, a double bond is introduced between the 7- and 8-positions of this compound, and an acyl group at its 3β-position (when an acyl group exists at the 1α-position the acyl group as well) is split off by hydrolysis. The introduction of the double bond is effected, for example, by brominating the compound of formula (IV) with N-bromosuccinimide to introduce a bromine atom into the carbon atom at the 7-position, and thereafter dehydrobrominating the brominated compound. The reaction of the compound of formula (IV) with N-bromosuccinimide can be carried out by heating them at the refluxing temperature in an inert gaseous atmosphere in a solvent such as carbon tetrachloride.

The dehydrobromination of the 7-brominated compound may be carried out by a method known per se, for example by treating it with tetra-n-butyl ammonium fluoride at room temperature in the presence of a catalytic amount of tetra-n-butyl ammonium bromide in a solvent such as tetrahydrofuran in an atmosphere of an inert gas while shutting off light.

The resulting 5,7-diene compound is hydrolyzed to split off the acyl group at the 3β-position and if present, the acyl group at the 1α-position. Hydrolysis can be carried out by a method known per se, for example by treating the 5,7-diene compound with an alcohol solution of an alkali hydroxide such as potassium hydroxide and sodium hydroxide.

The resulting compound of formula (V) can be converted into the 24,24-difluoro-26,27-dimethyl vitamin $D_3$ derivative of formula (I) by irradiation of ultra-violet light.

The ultraviolet light irradiation of the compound of formula (V) can be carried out by dissolving it in a suitable solvent, preferably a low-boiling solvent, and irradiating the solution with ultraviolet light. Examples of suitable solvents are hydrocarbons such as hexane, octane and benzene, ethers such as diethyl ether and tetrahydrofuran, alcohols such as methanol and ethanol, preferably lower alkanols, and mixtures thereof. The effective wavelength of ultraviolet light used for irradiation is from 200 to 360 nm. Lights of any light sources are available if they include the ultraviolet light having the wavelengths in the above range. Examples of suitable light sources are a medium-pressure mercury lamp, a high-pressure mercury lamp and laser beams. If required, unwanted lights may be cut through a filter. The time for irradiation of ultraviolet light varies with the intensity of a lamp as a light source and the scale of reaction, and is properly selected from a range of between several tens of seconds and several hours.

The irradiation is performed at temperatures in the range of usually from about −20° to about 120° C., preferably from about −10° to about 30° C., in an atmosphere of preferably an inert gas.

After the irradiation, the solution is kept in an inert gaseous atmosphere at temperatures from room temperature to the reflux temperature, preferably the reflux temperature, for 1 to 2 hours to give a 24,24-difluoro-26,27-dimethyl vitamin $D_3$ derivative.

The product can be separated from the reaction mixture and purified by a method known per se, such as chromatography, extraction or recrystalliztion.

The compound of formula (II) used as a starting compound in the process steps shown in reaction scheme A can be synthesized by using a known compound of formula (VI) or (VII).

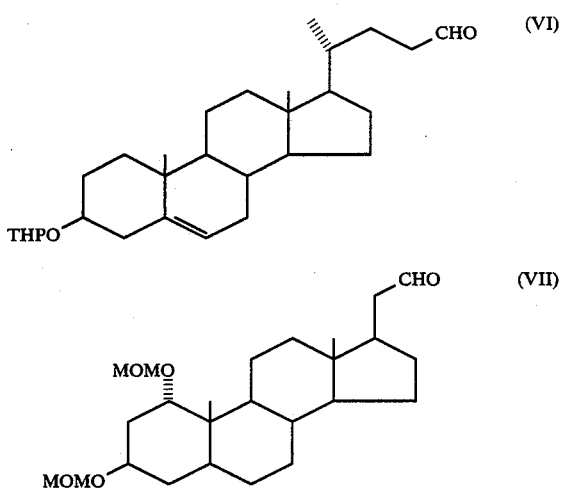

In the formulae, THP represents a tetrahydropyranyl group, and MOM, a methoxymethyl group.

A compound of formula (II) in which $Y^1$ is a hydrogen atom can be obtained by reacting the compound of formula (VI) with a tris(methylthio)methyl anion, treating the product with an acid to remove the tetrahydropyranyl group (THP) to form a diol, selectively acylating the diol with an acyl chloride in pyridine to form a 3β-acyloxy-24-ol compound, hydrolyzing the resulting compound with mercuric chloride/mercuric oxide in an aqueous lower alkanol, particularly aqueous methanol to obtain an -hydroxy ester, and oxidizing the ester by the method of Swern et al. [J. Org. Chem., vol. 43, page 2480 (1975)].

A compound of formula (II) in which $Y^1$ is an acyloxy group can be obtained by subjecting the compound of formula (VII) and methylenetriphenylphosphorane to the Wittig reaction, selectively hydroborating the resulting product with 9-borabicyclo[3,3,1]nonane, oxidizing the product with hydrogen peroxide under alkaline conditions to form a 23-ol compound, oxidizing the 23-ol compound by the method of Swern et al. to form a 23-aldehyde compound, removing the methoxymethyl group (MOM) from the aldehyde compound, acylating the resulting compound, thereafter treating the product with an anion obtained from a phosphonoacylate derivative of the following formula

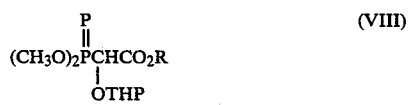

wherein R and THP are as defined above, and n-butyllithium to form an enol ether, and treating it with an acid.

The 24,24-difluoro-26,27-dimethyl vitamin $D_3$ derivatives provided by this invention have excellent bone forming activity in mammals, and is less toxic. Accordingly, the compound of this invention is useful as a medicament for the prevention and/or treatment of various diseases caused by abnormality and disorders of calcium balance and calcium absorption, such as calcium pathobolism and osteoporosis.

The excellent activity of the compound of this invention can be demonstrated by the following animal test.

Measurement of bone forming activity in a rat osteoporosis model

Test animals

Wistar-strain female rats (28 to 32 weeks old) were purchased. Eleven weeks later (39 to 43 weeks old), the rats got ovariectomy and sciatic neurotomy under pentobarbital anesthesia. Thus, experimental osteoporosis was induced. Ten rats per group were used.

Experimental method

From 3 to 7 days after the operation, a test compound dissolved in Panacede 810 was orally administered to rats over the course of 10 weeks at a dose of 0.5 ml per day per kg of body weight four times a week (on Monday, Tuesday, Thursday, Friday). On the day next to the day of final administration of the test compound, the femur was removed, defatted with ethanol and ether, dried at 110° C. for 16 hours, and ashed at 900° C. for 16 hours. The amount of calcium in the ash was measured by atomic absorption spectrophotometry (the amount of bone calcium). The amount of inorganic phosphorus in the ash (the amount of bone inorganic phosphorus) was measured by the Fiske-Subbarrow method [C. H. Fiske and YU. Subbarrow: J. Biol. Chem., 66, 375 (1925)].

Shimadzu double beam atomic absorption spectrophotomery AA-650 was used in atomic absorption spectrophotometry, and Hitachi 500-type automatic analyzer was used in the Fiske-Subbarrow method.

The test compounds and doses are shown in Table 1. In Table 1, the control is a vehicle for the test compound. Compound A is 1α,25-dihydroxy-24,24-difluoro-26,27-dimethyl vitamin $D_3$.

Test results

The results are summarized in Table 1. It is seen that compound A of this invention showed an activity of markedly increasing the amount of bone calcium and the amount of bone inorganic phosphorus, and excellent bone forming activity.

TABLE 1

| Test compound | Dose (pmole/kg) | Amount of bone Ca* (mg) | Amount of bone inorganic P* (mg) |
|---|---|---|---|
| Control | 0 | 120.4 ± 3.36 | 62.3 ± 1.57 |
| Compound A | 200 | 138.8 ± 4.00 | 72.3 ± 1.90 |

*The values are the average ± standard error.

For use as a medicament for the prevention and/or treatment of diseases such as calcium pathobolism and osteoporosis, the compound of this invention may be administered to mammals in a dose of about 25 to about 400 ng/day, preferably about 50 to 200 ng/day. This dose range, however, is a provisional criterion, and the compound may be administered in doses outside this range by a physician's judgement depending upon the condition, sex, age and weight, for example, of a patient. The adminstration may be effected orally or parenterally through various routes (e.g., subcutaneous, intramuscular, intravenous, intraperitoneal, and intrarectal).

The compound of this invention may be formulated into a dosage form according to the route of administration. For example, for oral administration, it can be formulated into tablets, capsules, granules, powders, syrups, elixirs, etc. For parenteral administration, it can be formulated into injectable preparations, drops, suppositories, etc. A pharmaceutical composition in such dosage forms may be prepared by mixing an effective amount of the compound of this invention with a pharmaceutically acceptable carrier or diluent (adjuvant) and formulating the mixture into the desired dosage form in a usual manner.

Illustrative of the adjuvant which may be incorporated in solid preparations such as tablets, capsules, granules and powders are binders such as tragacanth gum, acacia, corn starch or gelatin; excipients such as dicalcium phosphate; disintegrants such as corn starch, potato starch or alginic acid; lubricants such as magnesium stearate; sweetening agents such as sucrose, lactose or saccharin; and flavoring agents such as peppermint, oil of wintergreen or cherry. Various other materials may be present as coatings or in order to otherwise modify the physical form of the dosage unit. For example, tablets may be coated with shellac, sugar, or both. The syrup or elixir may contain the active compound, sucrose as a sweetening gent, methyl and propyl parabvens as preservatives, a dye and a cherry or orange flavor.

Sterile compositions for injection can be formulated according to the conventional practice of pharmaceutical preparation by dissolving or suspending the active compound in a vehicle such as water for injection, a natural vegetable oil such as sesame oil, coconut oil, peanut oil or cottonseed oil, or a synthetic fatty vehicle such as ethyl oleate. Buffers, preservatives, antioxidants and the like may be incorporated as required.

The following Examples illustrate this invention in more detail.

EXAMPLE 1

(a) Synthesis of 3β,24ξ-dihydroxy-24-tris(methyl-thio)methylchol-5-ene

Under an argon atmosphere at $-78°$ C., 10.4 ml (17.7 mmoles) of a hexane solution of n-butyllithium was added to a solution of 2.4 ml (18.0 mmoles) of tris(methylthio)methane in 40 ml of tetrahydrofuran (THF for short), and the mixture was stirred for 40 minutes at the same temperature. To the mixture was added dropwise 15 ml of a THF solution of 798 mg (1.8 mmoles) of 3β-hydroxychol-5-en-24-al [compound of formula (VI)], and the mixture was stirred at $-78°$ C. for 40 minutes. The mixture was extracted with ether in a customary manner, and the resulting residue was dissolved in a mixture of 10 ml of THF and 5 ml of methanol. Four drops of 2N hydrochloric acid was added, and the mixture was stirred at room temperature for 100 minutes. The mixture was extracted with ether in a customary manner, and the resulting crude product was purified by silica gel column chromatography [31 g; eluted with hexane/ethyl acetate (10:1)] to give 651 mg of the captioned compound having a melting point of 141° to 143° C. (recrystallized from methanol).

(b) Synthsis of 3β-acetoxy-24-tris(methylthio)methylchol-5-en-24ξ-ol

The 3β,24ξ-diol compound obtained in (a) above (103 mg; 0.20 mmole) was dissolved in 0.5 g of pyridine, and 15.6 microliters (0.22 mmole) of acetyl chloride was added. The mixture was stirred at room temperature for 50 minutes. The mixture was extracted with ether in a customary manner. The resulting crude product was purified by silica gel column chromatography [14 g; eluted with hexane/ethyl acetate (10:1)] to give 77 mg of the captioned acetoxy compound having a melting point of 139° to 141° C. (recrystallized from methanol).

(c) Synthesis of methyl 3β-acetoxy-24ξ-hydroxychol-5-ene-24-carboxylate

A mixture of 287 mg (0.52 mmole) of the 24 ξ-ol compound obtained in (b) above, 447 mg (1.65 mmoles) of mercuric chloride and 151 mg (0.71 mmole) of mercuric oxide was stirred at room temperature for 2 hours in aqueous methanol (methanol:water=12:1). The reaction mixture was suction-filtered, and the residue was washed with dichloromethane. The filtrate was extracted with ether. The organic layer was washed with a saturated aqueous solution of ammonium acetate, and worked up in a customary manner. The resulting crude product was purified by silica gel column chromatography [29 g; eluted with hexane/ethyl acetate(5:1)] to give 230 mg of the captioned methyl carboxylate having a melting point of 120° to 122° C. (recrystallized from hexane).

(d) Synthesis of methyl 3β-acetoxy-24-oxochol-3-ene-24-carboxylate

Dimethyl sulfoxide (0.13 ml; 0.91 mmole) was added to 4 ml of a dichloromethane solution of 0.08 ml (0.91 mmole) of oxalyl chloride at $-78°$ C. in an atmosphere of argon, and the mixture was stirred for 10 minutes under the same conditions. To the solution was added 5 ml of a dichloromethane solution of 217 mg (0.47 mmole) of the 24ξ-ol compound obtained in (c) above, and the mixture was stirred for 15 minutes. Triethylamine (0.52 ml; 3.75 mmoles) was added, and the mixture was stirred for 5 minutes. Then, the temperature of the reaction mixture was returned to room temperature. The mixture was extracted with ether in a customary manner, and the resulting crude product was purified by silica gel column chromatography [31 g; eluted with hexane/ethyl acetate (5:1)] to give 148 mg of the captioned α-keto ester [compound of formula (II) in which $Y^1$ is H] having a melting point of 140° to 142° C. (recrystallized from hexane/ethyl acetate).

(e) Synthesis of methyl 3-acetoxy-24,24-difluorochol-5-ene-24-carboxylate (Diethylaminosulfur) trifluoride (DAST) (1.8 ml; 13 mmoles) was added at 0° C. in an argon atmosphere to a solution of 848 mg (1.85 mmoles) of methyl 3β-acetoxy-24-oxochol-5-ene-24-carboxylate, and the mixture was stirred at room temperature for 45 hours. The mixture was extracted with ethyl acetate in a customary manner, and the resulting crude product was purified by silica gel column chromatography [109 g; eluted with hexane/ethyl acetate (20:1)] to give 802 mg of the captioned 24,24-difluoro compound having a melting point of 125° to 127° C. (recrystallized from hexane).

(f) Synthesis of 3β-acetoxy-24,24-difluoro-26,27-dimethylcholest-5-en-25-ol

An ethyl lithium solution (6.5 ml; about 8.5 mmoles) prepared from 1.9 ml (25 mmoles) of ethyl bromide and 0.75 g (about 110 mmoles) of lithium was added at 0° C. in an argon atmosphere to 7 ml of a THF solution of 80 mg (0.17 mmole) of methyl 3β-acetoxy-24,24-difluorochol-5-ene-24-carboxylate, and the mixture was stirred for 1.5 hours under the same conditions. The mixture was extracted with ethyl acetate in a customary manner, and the resulting residue was stirred at room temperature for 12 hours with 0.5 ml of acetic anhydride in 0.5 ml of pyridine, and then extracted with ethyl acetate in a customary manner by silica gel column chromatography [4.6 g; hexane/ethyl acetate (20:1)] to give 62 mg of the captioned 26,27-dimethyl compound having a melting point of 127° to 128° C. (recrystallized from methanol).

(g) Synthesis of 24,24-difluoro-3β,25-dihydroxy-26,27-dimethylcholesta-5,7-diene A mixture of 25.8 mg (0.051 mmole) of 3β-acetoxy-24,24-difluoro-26,27-dimethylcholest-5-ene-25-ol and 12.7 mg (0.017 mmole) of N-bromosuccimide was heated under reflux for 25 minutes in 3.5 ml of carbon tetrachloride in an atmosphere of argon. The reaction mixture was cooled to 0° C. The precipitate formed was separated by filtration, and the solvent was evaporated from the filtrate. The resulting residue was dissolved in 4 ml of THF, and a catalytic amount of tetra-n-butyl ammonium bromide was added. The mixture was stirred for 50 minutes in an atmosphere of argon while shutting off light. Then, 0.16 ml (0.16 mmole) of a 1M THF solution of tetra-n-butyl ammonium fluoride was added and the mixture was stirred for 30 minutes under the same conditions. The mixture was extracted with ethyl acetate in a customary manner, and the resulting crude product was purified by thin-layer silica gel chromatography (developing solvent: hexane/ethyl acetate=10:1; developed three times) to give 11.3 mg of the acetate. It was dissolved in 4 ml of THF, and 1 ml of a 5% methanol solution of potassium hydroxide was added. The mixture was stirred at room temperature for 30 minutes in an atmosphere of argon while shutting off light. The mixture was extracted with ethyl acetate in a customary manner, and the resulting crude product was purified by thin-layer silica gel chromatography (developing solvent: hexane/ethyl acetate=4:1; developed four times) to give 9.3 mg of the captioned 5,7-diene compound.

UV $\lambda_{max}^{EtOH}$: 294, 282, 272 nm.

(h) Synthesis of 24,24-difluoro-25-hydroxy-26,27-dimethyl vitamin $D_3$ 9.3 mg of 24,24-difluoro-3β,25-dihydroxy-26,27-dimethylcholesta-5,7-diene was dissolved in a mixture of 90 ml of benzene and 40 ml of ethanol, and in an argon stream at 0° C., the solution was irradiated with ultra-violet light for 7 minutes using a medium-pressure mercury lamp through a Vycor filter. Subsequently, the reaction mixture was heated under reflux for 1 hour in at atmosphere of argon. The solvent was evaporated under reduced pressure, and the resulting crude product was purified by thin-layer silica gel chromatography (developing solvent: benzene/ethyl acetate=10:1; developed four times) to give 2.6 mg of the captioned vitamin $D_3$ derivative [the compound of formula (I) in which X is H].

UV $\lambda_{max}^{EtOH}$: 265 nm, $\lambda_{min}^{EtOH}$: 228 nm.

EI-MS (70 eV) m/z: 464 (M, 32, 3), 446 (9, 1), 444 (2, 8), 431 (23, 3), 271 (17, 2), 253 (21, 6), 175 (6, 9), 173 (10, 1), 155 (11, 2), 136 (76, 5), 118 (base peak), 87 (37, 1), 6.9 (4, 5).

EXAMPLE 2

(a) Synthesis of 1α,3β-dimethoxymethoxy-22-norchol-5,22-diene

In an argon stream at 0° C., 1.9 ml (3.23 mmoles) of a 1.7M hexane solution of n-butyllithium was added to 12 ml of a THF suspension of 1.4 g (3.45 mmoles) of methyltriphenyl phosphonium iodide, and the mixture was stirred for 50 minutes. To the mixture was added dropwise at 0° C. 8 ml of a THF solution of 1.0 g (2.32 mmoles) of the compound (VII), and the mixture was stirred at room temperature for 30 minutes. The mixture was extracted with ether in a customary manner, and the resulting product was purified by silica gel column chromatography [57 g; eluted with hexane/ethyl acetate (5:1)] to give 0.97 g of the captioned diene compound as an oil.

(b) Synthesis of 1α,3β-dimethoxymethoxy-22-norchol-5-en-23-ol

To 5 ml of a THF solution of 393 mg (0.91 mmole) of the 1α,3β-dimethoxymethoxy-22-norchol-5,22-diene obtained in (a) above was added dropwise 3.8 ml (1.8 mmoles) of a 0.5M THF solution of 9-borabicyclo[3,3,1]-nonane in an atmosphere of argon at 0° C. After the addition, the reaction solution was stirred at room temperature for 45 hours. To the solution was added 0.4 ml of a 3N aqueous solution of sodium hydroxide, and subsequently, 0.4 ml of a 30% aqueous solution of hydrogen peroxide at 0° C. The mixture was stirred at the same temperature for 35 minutes. The mixture was extracted with ether in a customary manner. The resulting crude product was purified by silica gel column chromatography [85 g; eluted with hexane/ethyl acetate (3:1)] to give 252 mg of the captioned 23-ol compound having a melting point of 107° to 109° C. (recrystallized from hexane).

(c) Synthesis of 1α,3β-dimethoxymethoxy-22-norchol-5-en-23-al

Dimethyl sulfoxide (0.41 ml; 5.79 mmoles) was added to 10 ml of a dichloromethane solution of 0.28 ml (2.88 mmoles) of oxalyl chloride at −78° C. in an atmosphere of argon, and the mixture was stirred for 10 minutes under the same conditions. To the mixture was added 6 ml of a dichloromethane solution of 850 mg (1.44 mmoles) of 1α,3β-dimethoxymethoxy-22-norchol-5-en-23-ol, and the mixture was stirred for 15 minutes. Triethylamine (1.6 ml; 11.5 mmoles) was added, and the mixture was stirred for 5 minutes. Then, the temperature of the reaction mixture was returned to room temperature. The reaction mixture was extracted with ether in a customary manner. The resulting crude product was purified by silica gel column chromatography [40 g; hexane/ethyl acetate (4:1)] to give 579 mg of the captioned aldehyde as an oil.

(d) Synthesis of 1α,3β-diacetoxy-22-norchol-5-en-23-al 6N hydrochloric acid (2.4 ml) was added to 8 ml of a THF solution of 579 mg (1.3 mmoles) of 1α,3β-dimethoxymethoxy-22-norchol-5-en-23-al, and the mixture was stirred at 60° C. for 60 minutes. The mixture was extracted with ethyl acetate in a customary manner. The resulting residue was dissolved in 3 ml of pyridine, and stirred with 1 ml of acetic anhydride at room temperature for 20 hours. The mixture was extracted with ethyl acetate in a customary manner, and the resulting crude product was purified by silica gel column chromatography [37; eluted with hexane/ethyl acetate (4:1)] to give 258 mg of the captioned diacetate compound having a melting point of 135° to 137° C. (recrystallized from hexane/ethyl acetate).

(e) Synthesis of methyl 1α,3β-diacetoxy-24-oxochol-5-en-24-carboxylate

To 1.5 ml of a THF solution of 0.13 ml (1.12 mmoles) of diisopropylamine was added 0.6 ml (1.02 mmoles) of an n-butyl lithium solution at −78° C. in an atmosphere of argon. The mixture was stirred for 30 minutes to prepare an LDA solution. To the solution was added 4 ml of a THF solution of 310 mg (1.10 mmoles) of the phosphonoacetate [the complound of formula (VIII) in which R is methyl], and the mixture was stirred at −78° C. for 30 minutes. Then, 4 ml of a THF solution of 377 mg (0.85 mmole) of the 1α,3β-diacetoxy-22-norchol-5-en-23-al obtained in (c) above, and the mixture was stirred at room temperature for 2.5 hours. The mixture was extracted with ether in a customary manner. The resulting crude enol ether was dissolved in a mixture of 4 ml of THF and 4 ml of methanol, and 20 mg of p-toluenesulfonic acid was added. The mixture was stirred at room temperature for 40 minutes. The mixture was extracted with ether in a customary manner, and the resulting crude product was purified by silica gel column chromatography [40 g; eluted with hexane/ethyl acetate (7:1)] to give 225 mg of the captioned α-keto ester (1) [the compound of formula (II) in which $Y^1$ is acetoxy] as an oil.

(f) Synthesis of methyl 1α,3β-diacetoxy-24,24-difluorochol-5-en-24-carboxylate

By the same operation as in Example 1, (e), the captioned difluoro compound (as an oil) was obtained from the methyl 1α,3β-diacetoxy-24-oxochol-5-ene-24-carboxylate obtained in (e) above.

(g) Synthesis of 1α,3β-diacetoxy-24,24-difluoro-26,27-dimethylcholest-5-en-25-ol By the same operation as in Example 1, (f), the captioned dimethyl compound (as an oil) was obtained from methyl 1α,3β-diacetoxy-24,24-difluoro-5-ene-25-carboxylate obtained in (f) above.

(h) Synthesis of 24,24-difluoro-26,27-dimethyl-1α,3β,25-trihydroxycholesta-5,7-diene By the same operation as in Example 1, (g), the captioned 5,7-diene compound was obtained from 1α,3β-diacetoxy-24,24-difluoro-26,27 -dimethylcholest-5-en-25-ol obtained in (g) above.

UV $\lambda_{max}^{EtOH}$: 294, 282, 271, 262 nm.

(i) Synthesis of 1α,25-dihydroxy-24,24-difluoro-26,27-dimethyl vitamin $D_3$

The 24,24-difluoro-26,27-dimethyl-1α,3β,25-trihydroxycholesta-5,7-diene (1.0 mg) was dissolved in a mixture of 90 ml of benzene and 40 ml of ethyl acetate, and the solution was irradiated for 3 minutes with ultraviolet light in an argon atmosphere at 0° C. using a medium-pressure mercury lamp. The reaction mixture was heated under reflux for 1 hour in an argon atmosphere. The solvent was evaporated under reduced pressure, and the resulting crude product was purified by thin-layer silica gel chromatography (developing solvent: benzene/ethyl acetate=1:1; developed three times) to give 202 micrograms of the captioned vitamin $D_3$ derivative [the compound of formula (I) in which X is OH).

UV $\lambda_{max}^{EtOH}$: 265 nm, $\lambda_{min}^{EtOH}$: 228 nm.

EI-MS (70 eV) m/z: 480 (M, 8, 1), 462 (75, 2), 444 (37, 0), 429 (3, 6), 287 (5, 1), 269 (28, 7, 10, 7), 251 (17, 1), 236 (4, 1), 155 (31, 0), 152 (22, 0). 134 (base peak), 116 (4,5), 87 (38, 5), 69 (4,5)

What is claimed is:

1. A 24,24-difluoro-26,27-dimethyl vitamin $D_3$ derivative represented by the formula:

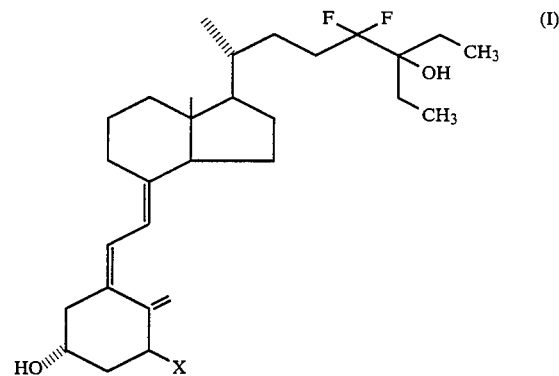

wherein X represents a hydroxyl group.

2. A pharmaceutical composition for the prevention or treatment of calcium pathobolism or osteoporosis, which comprises an amount, effective for the prevention or treatment of said diseases, of a 24,24-difluoro-26,27-dimethylvitamin $D_3$ derivative of claim 1, and a pharmaceutically acceptable diluent or carrier.

3. A method for the prevention or treatment of calcium pathobolism or osteoporosis, which comprises administering an effective amount of a 24,24-difluoro-26,27-dimethylvitamin $D_3$ derivative of claim 1 to a mammal.

* * * * *